United States Patent
Tsujii

(10) Patent No.: US 7,212,602 B2
(45) Date of Patent: May 1, 2007

(54) X-RAY IMAGE PROCESSING APPARATUS AND X-RAY IMAGE PROCESSING METHOD

(75) Inventor: Osamu Tsujii, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 127 days.

(21) Appl. No.: 11/049,840

(22) Filed: Feb. 3, 2005

(65) Prior Publication Data

US 2005/0175140 A1 Aug. 11, 2005

(30) Foreign Application Priority Data

Feb. 5, 2004 (JP) ............................. 2004-028891

(51) Int. Cl.
*H05G 1/10* (2006.01)

(52) U.S. Cl. ........................................................ 378/8

(58) Field of Classification Search .................. 378/95, 378/8, 4–20, 62, 91–97, 210, 901
See application file for complete search history.

(56) References Cited

U.S. PATENT DOCUMENTS

| | | | |
|---|---|---|---|
| 6,061,421 A | 5/2000 | Hagiwara ...................... | 378/4 |
| 6,061,422 A | 5/2000 | Miyazaki et al. ............. | 378/15 |
| 6,072,851 A | 6/2000 | Sivers .......................... | 378/15 |
| 6,480,560 B2 | 11/2002 | Hsieh ........................... | 378/8 |
| 7,006,593 B2 * | 2/2006 | Kokubun et al. ............. | 378/8 |
| 7,085,342 B2 * | 8/2006 | Younis et al. ................. | 378/8 |

FOREIGN PATENT DOCUMENTS

JP 2000-217810 A 8/2000

OTHER PUBLICATIONS

Wang et al., A Knowledge-based Cone-beam X-ray CT Algorithm for Dynamic Volumetric Cardiac Imaging, Med. Phys. 29 (8), Aug. 2002.*
L. A. Feldkamp, et al. "Practical Cone-Beam Algorithm", J.Opt. Soc. Am. A/vol. 1, No. 6, p. 612-619, Jun. 1984.

* cited by examiner

*Primary Examiner*—Edward J. Glick
*Assistant Examiner*—Alexander Taningco
(74) *Attorney, Agent, or Firm*—Canon USA. Inc., IP Division

(57) ABSTRACT

When photographing is started, pulsation of a subject is detected and a pulsation period T is measured. A standstill period is determined and the rotation time S of a rotation table is calculated according to the equation S=nT (where n denotes an odd number). When rotation is started and a predetermined speed and a predetermined angle are attained, X-ray exposure is started, and the exposure is stopped when a predetermined number of views are obtained. After scan data is collected, a motion area is detected and data-rearrangement is performed, and a half-scan reconstructed image is created by using the rearranged scan data. When an artifact is identified by reconstructed-image evaluation, a retry is made. Subsequently, a standstill period is changed, the data rearrangement is performed again, and half-scan reconstruction and image evaluation are performed again. When the image evaluation is successful, three-dimension-voxel coupling is performed.

8 Claims, 8 Drawing Sheets

X-RAY IMAGE PROCESSING APPARATUS AND X-RAY IMAGE PROCESSING METHOD

BACKGROUND OF THE INVENTION

1. Field of the Invention

The present invention relates to an X-ray image processing apparatus for creating the image of an X-ray characteristic distribution in a subject by using ordinary rays, such as an X-ray computer tomography (CT) apparatus for photographing an image by using X-rays or the like, and an X-ray image processing method.

2. Description of the Related Art

Hitherto, known X-ray CT apparatuses for exposing a subject to X-rays, detecting an X-ray that passes through the subject or that is scattered by the subject using an X-ray detector, and picking up the fluoroscopic image, tomographic image, and three-dimensional image of the subject based on the X-ray detection output (the number of photons of the X-ray) have been used.

However, the subject must be fixed for collecting data obtained during scanning performed by the X-ray CT apparatus. Further, the body motion and/or the internal-organ motion during the scanning generates an artifact in a reconstructed image. Subsequently, the diagnostic efficiency reduces.

Japanese Patent Laid-Open No. 2000-217810 and Japanese Patent Laid-Open No. 2002-355241 disclose cone-beam CT apparatuses, as known systems for solving the above-described problems. The cone-beam CT apparatuses obtain a transmission X-ray image of the subject by emitting an X-ray to the subject from circumference, and create and display an X-ray tomography image and/or a three-dimensional X-ray image of the subject based on the transmission X-ray image. According to the above-described disclosures, the transmission X-ray images are divided into different groups, and a transmission X-ray image corresponding to each group is reconstructed, so that a plurality of X-ray distribution images is obtained. Then, the sharpness of each of the X-ray distribution images is calculated and an X-ray tomography image and/or a three-dimension X-ray image of the subject is created, based on the transmission X-ray image of a group showing the highest sharpness, and displayed. More specifically, various half-scan data sets with shifted start angle are generated from full-scan data. Then, reconstructed images created by using the various half-scan data sets are compared to one another and a suitable image is selected.

An imaging system may be used for solving the above-described problems. The imaging system scans the heart of a patient, obtains a plurality of projection views, and determines a differential projection by the projection views. A load function for minimizing the motion artifact is used for the differential projection, and an inequality index used for determining the image reconstruction position is determined by the differential projection. According to this method, an electrical signal is not measured but the dynamic motion of the heart is directly measured. Further, the most suitable position for minimizing an image artifact is selected by using the projection data. More specifically, by using the load function for the differential projection, as disclosed in Japanese Patent Laid-Open No. 2002-355241, the heart-pulsation phase can be detected. Subsequently, a reconstructed image is obtained by using half-scan data from which images showing major heart-pulsation motion are moved.

The cone-beam CT apparatus have been developed, as X-ray CT apparatuses. In the case of the known X-ray CT apparatuses, an X-ray beam is sliced in a vertical direction Z and referred to as a fan beam. However, in the case of the cone-beam CT (CBCT), an X-ray beam extending in the direction Z is used. Therefore, the X-ray beam is referred to as a cone beam.

In the CBCT apparatus that is different from known CT apparatuses wherein a small number of slices are collected at the same time, several hundred slices of data are collected at the same time. That is to say, the projection data includes part inducing artifacts and another part inducing no artifacts. In general, the quality of an image reconstructed by using the full-scan data is better than that of an image reconstructed by using the half-scan data. Therefore, even though an artifact occurs in part of the projection data, the entire projection data should not be reconstructed by half scanning from the viewpoint of making effective use of the projection data.

SUMMARY OF THE INVENTION

For solving the above-described problems, the present invention provides an X-ray image processing apparatus and an X-ray image processing method for defining a specified area in a photographing area, performing reconstruction for the specified area by using data different from that used for reconstruction for other areas.

According to an aspect of the present invention, there is provided an X-ray image processing method for creating three-dimension reconstructed image data by using plural projection image data. The X-ray image processing method includes a division step for dividing an area corresponding to the projection image data into at least one standstill area showing no body motion and at least one motion area showing the body motion based on the projection image data, and a reconstruction step for creating the three-dimension reconstructed image data by using the projection image data. Reconstruction for the standstill area is performed by full scanning by using the projection image data corresponding to 360-degree photographing directions, and reconstruction for the motion area is performed by half scanning by using the projection image data corresponding to 180-degree photographing directions.

According to another aspect of the present invention, there is provided a program for making a computer perform an X-ray image processing method for creating three-dimension reconstructed image data by using plural projection image data. The X-ray image processing method includes a division step for dividing an area corresponding to the projection image data into at least one standstill area showing no body motion and at least one motion area showing body motion based on the projection image data, a reconstruction step for performing reconstruction for the standstill area by full scanning by using the projection image data corresponding to 360-degree photographing directions, and a reconstruction step for performing reconstruction for the motion area by half scanning by selecting the projection image data corresponding to 180-degree photographing directions.

According to another aspect of the present invention, there is provided a computer readable storage medium storing a program for making a computer perform an X-ray image processing method for creating three-dimension reconstructed image data by using plural projection image data. The X-ray image processing method includes a division step for dividing an area corresponding to the projection image data into at least one standstill area showing no body motion and at least one motion area showing the body motion based on the projection image data. The X-ray image processing method further includes a reconstruction step for performing reconstruction for the standstill area by full scanning by using the projection image data corresponding to 360-degree photographing directions and a reconstruction step for performing reconstruction for the motion area by half scanning by using the projection image data corresponding to 180-degree photographing directions.

According to another aspect of the present invention, there is provided an X-ray image processing apparatus that includes an X-ray generator for generating at least one X-ray, a rotation table for rotating a subject in the X-ray in the X-ray image processing apparatus such that the at least one X-ray generated by the X-ray generator passes through the subject, a two-dimension detector for converting the X-ray passed through the subject into projection image data, a division unit for dividing an area corresponding to the projection image data into at least one standstill area showing no body motion and at least one motion area showing body motion based on the projection image data picked up by the two-dimension detector, and a reconstruction unit for creating three-dimension reconstructed image data by using the plural projection image data. Reconstruction for the standstill area is performed by full scanning by using the projection image data corresponding to 360-degree photographing directions, and reconstruction for the motion area is performed by half scanning by selecting the projection image data corresponding to 180-degree photographing directions.

Further features and advantages of the present invention will become apparent from the following description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Exemplary embodiments of the present invention will now be described in detail in accordance with the accompanying drawings.

Figure 1A:
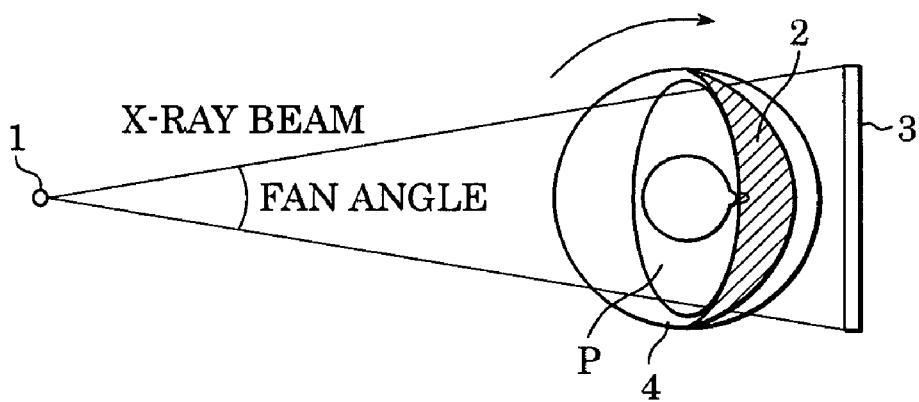
FIG. 1 shows the structure of an X-ray imaging apparatus.
Figure 1B:
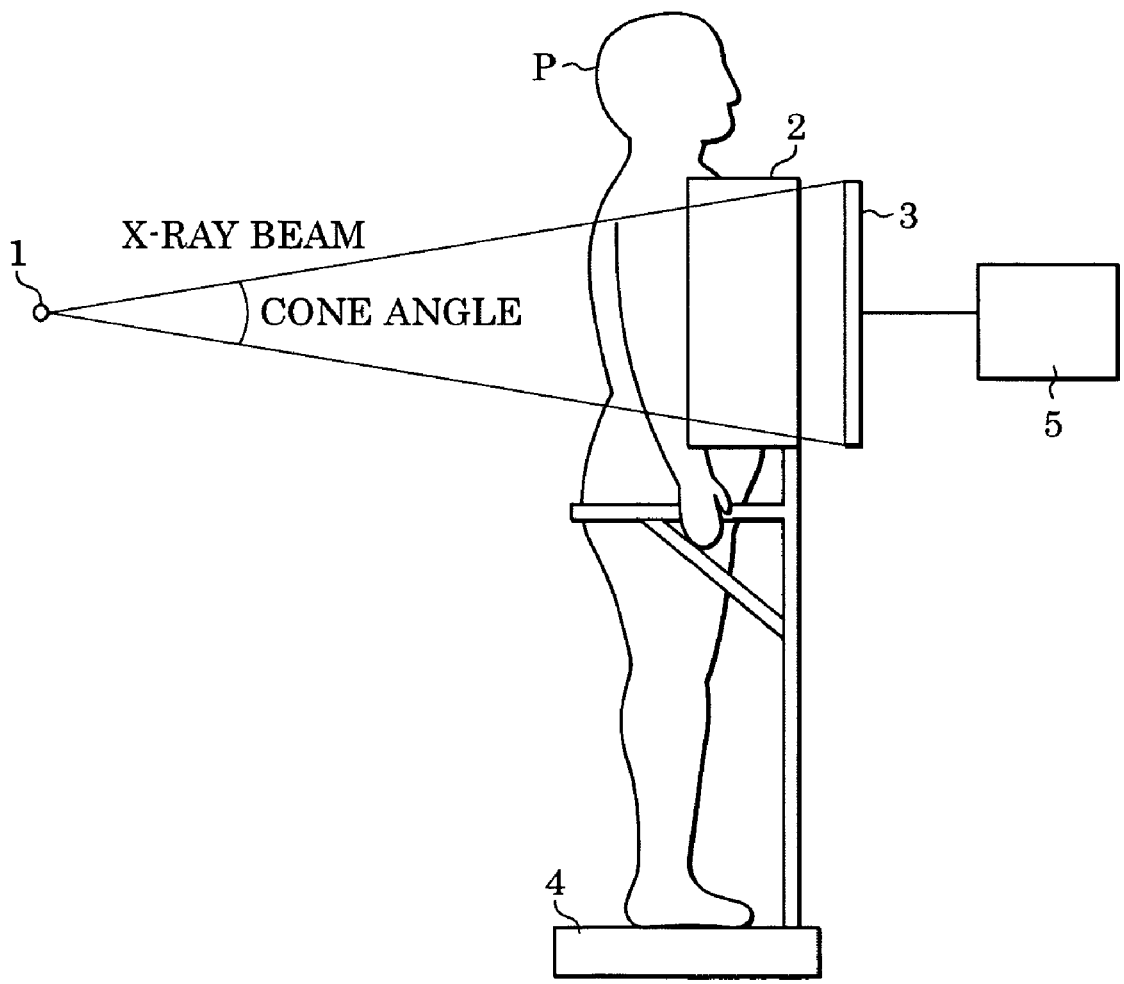

The present invention will be described in detail based on the embodiments shown in the drawings. FIG. 1A is a plan view of an X-ray imaging apparatus and FIG. 1B is a side elevation view of the same. A two-dimension detector 3 with a breast plate 2 provided toward the front is installed forward of an X-ray generator 1. A subject P on a rotation table 4 is placed forward of the breast plate 2. An output of the two-dimension detector 3 is connected to a reconstruction unit 5.

A fan angle and a cone angle are determined due to the geometrical arrangement of the X-ray generator 1 and the two-dimension detector 3. Since the two-dimension detector 3 is square-shaped in this embodiment, the fan angle and the cone angle are equivalent. In the two-dimension detector 3 including a semiconductor sensor, the size of a single pixel is 250×250 μm, the outer dimensions of the semiconductor sensor is 43×43 cm, and the number of pixels is 1720×1720.

An X-ray emitted from the X-ray generator 1 passes through the subject P placed on the rotation table 4, passes through the breast plate 2 and a scattered-radiation removal grid (not shown), and reaches the two-dimension detector 3. Data obtained by the two-dimension detector 3 is transferred to the reconstruction unit 5 and image reconstruction is performed.

Figure 2:
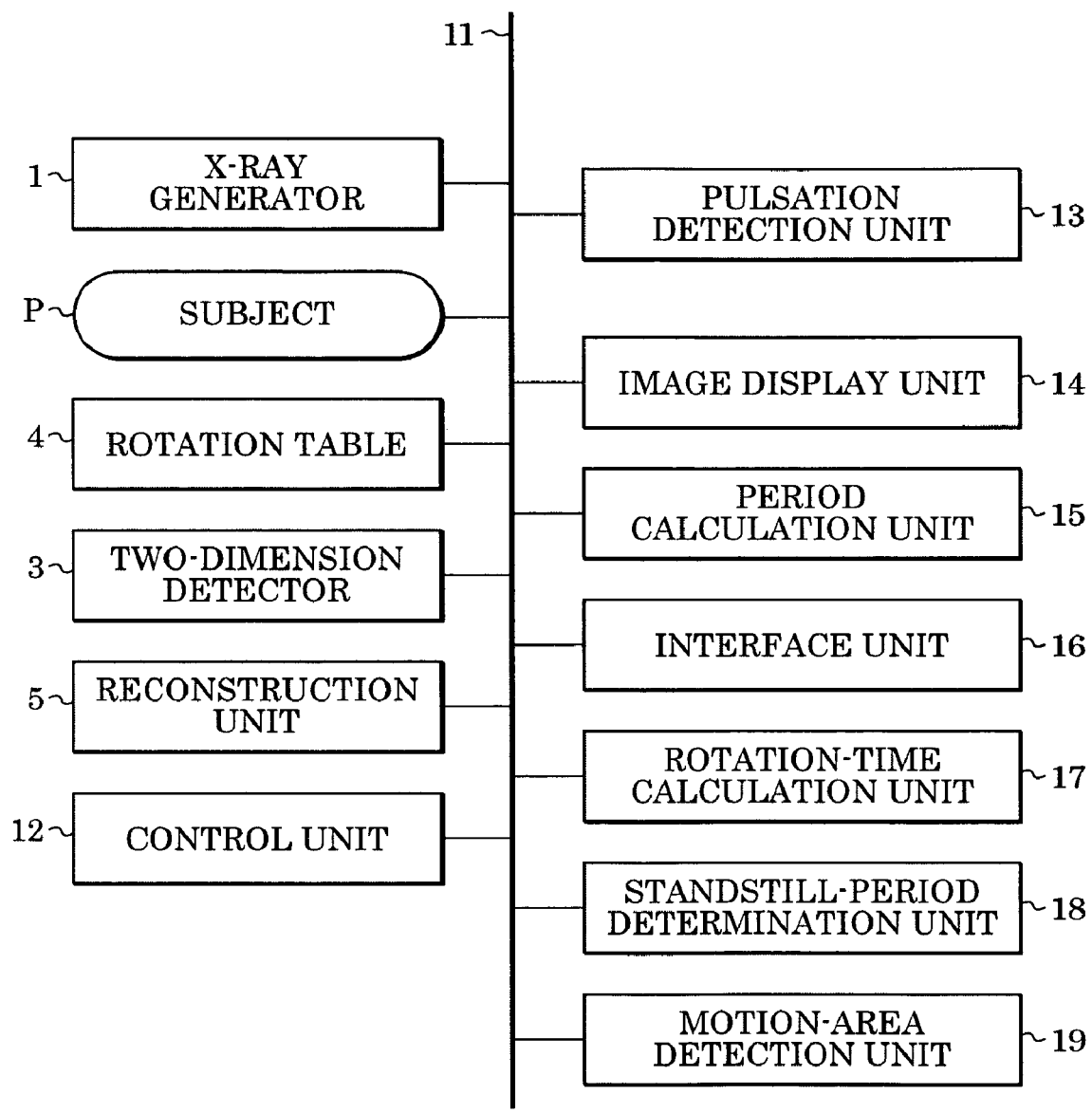
FIG. 2 is a block diagram of a system according to an embodiment of the present invention.

FIG. 2 shows a system block diagram. To a bus 11, the X-ray generator 1, the two-dimension detector 3, the rotation table 4, the reconstruction unit 5, a control unit 12, a pulsation detection unit 13, an image display unit 14, a period calculation unit 15, an interface unit 16, a rotation-time calculation unit 17, a standstill-period determination unit 18, and a motion-area detection unit 19 are connected. In practice, the entire system is formed, as a single computer. Therefore, the bus 11 functions, as an internal bus of the computer. Subsequently, a control signal and data are transmitted and received via the bus 11 and the control unit 12 functions, as a CPU of the computer.

Figure 3:
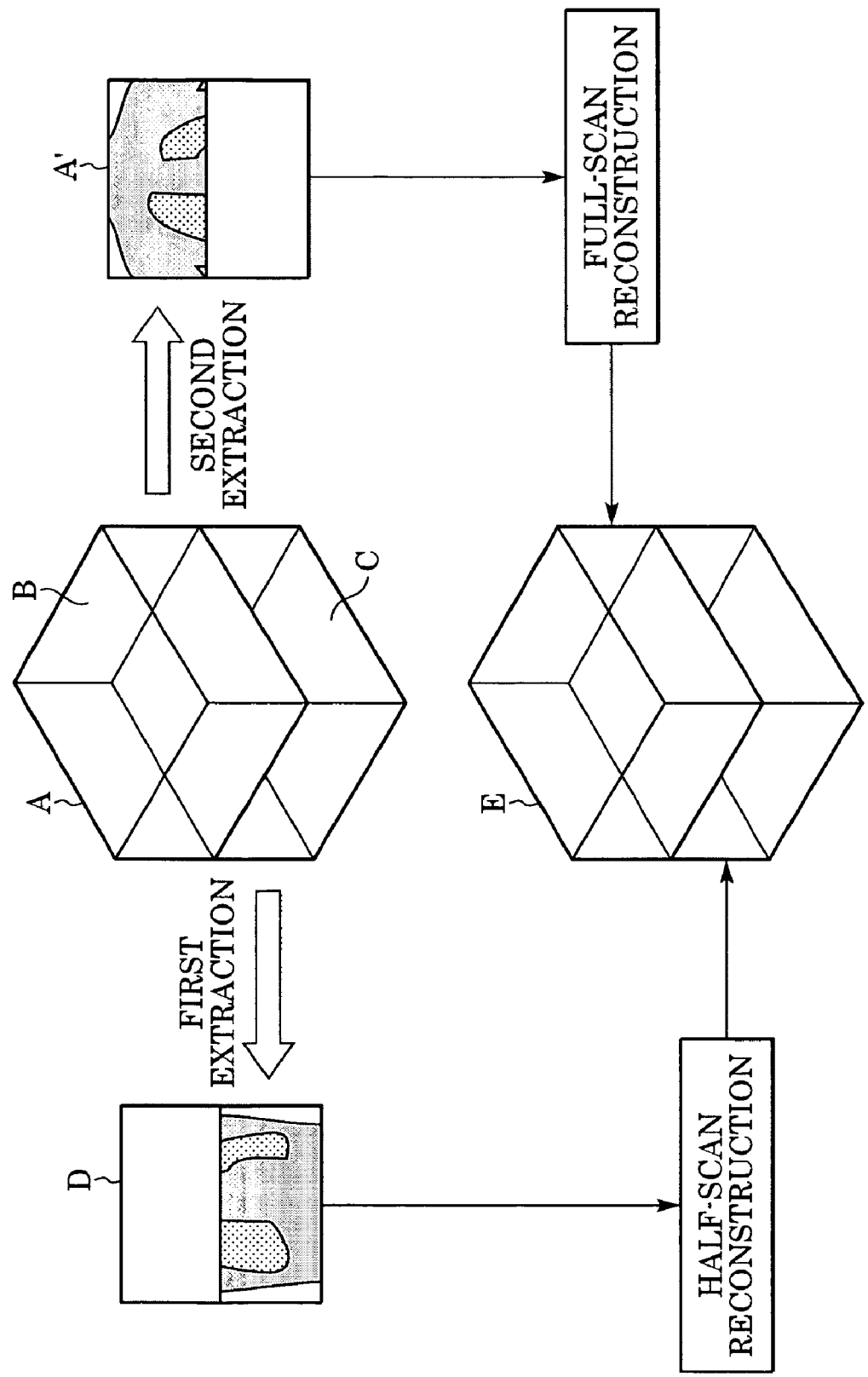
FIG. 3 is a conceptual illustration of the embodiment.

FIG. 3 is a conceptual illustration of the embodiment. Full data A of the subject P photographed by a CBCT apparatus is represented by a rectangular parallelepiped and the full data A is divided into a standstill area B and a motion area C by an analysis unit. The motion area C denotes an area showing the body motion, and an area showing involuntary motion of an internal organ (where the motion includes an oscillation, the motion is determined to be pulsation and where the internal organ in motion is a stomach, the motion is determined to be digestive motion.). If image reconstruction is performed by using the entire full-scan data forming the motion area C, an artifact may be reconstructed. Therefore, half data D is created by first data extraction and half-scan reconstruction is performed.

On the other hand, as for data forming the standstill area B, an image can be reconstructed by using the entire full data A. Therefore, full-scan reconstruction is performed by extracting full-data A' by the second data extraction. Then, three-dimension voxel data created by the reconstructed standstill area B is coupled to that of the reconstructed motion area C, and three-dimension voxel data E of the subject P is created.

Figure 5:
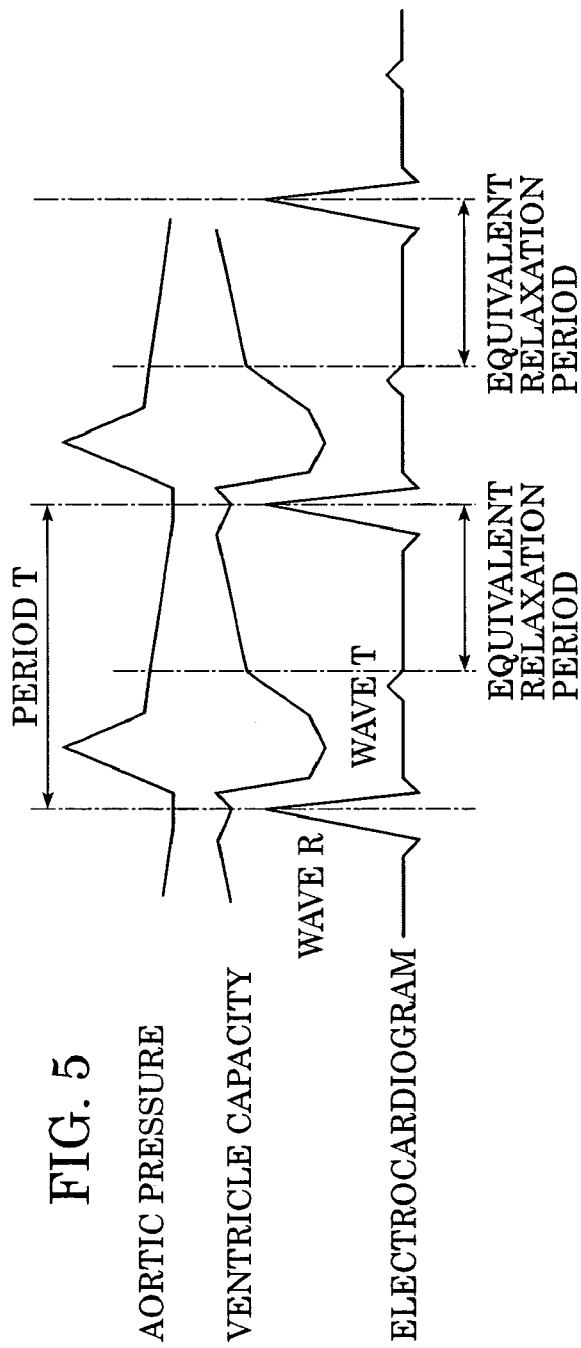
FIG. 5 illustrates an electrocardiograph waveform and heart contraction.

Processing procedures will be described according to a flowchart shown in FIG. 4, as below. First, an instruction to start photographing is issued via the interface unit 16 (step S101). Subsequently, the pulsation detection unit 13 detects the pulsation of the subject P (step S102). The pulsation detection unit may be an electrocardiograph, a pulse oximeter for detecting the oxygen saturation degree, or a morphological detection system. In the morphological detection system, the X-ray generator 1 performs X-ray exposure in succession, the two-dimension detector 3 receives the distribution of transmitted X-rays, and the size of a heart shown in an image is detected.

Where the electrocardiograph and the pulse oximeter are attached to the subject P, periodic heart-beat signals are detected. FIG. 5 shows a waveform detected by the electrocardiograph. The period-calculation unit 15 measures a pulsation period T by measuring time intervals between waves R of the waveform shown by the electrocardiograph (step S103). More specifically, the pulsation period T can be calculated by counting the number of reference pulses between a wave R and the next wave R.

Next, the standstill-period determination unit 18 determines a standstill period Q. The term standstill period Q denotes a period of time during which morphological changes hardly affect the heart pulsation, that is, an equivalent relaxation period. The standstill period Q is empirically determined with reference to a distinctive wave R. As shown in FIG. 5, the morphological change of a heart is divided into three periods including a contraction period, a relaxation period, and an equivalent relaxation period. The heart capacity expands during the relaxation period and the expansion converges during the equivalent relaxation period. Empirically, the latter half of the pulsation period T starting from a wave R can be substantially determined to be the equivalent relaxation period (step S104). However, the standstill period Q determined at step S104 is provisional and the standstill period Q is often changed, at step S112 that will be described later.

The pulse oximeter used in this embodiment can be easily attached to the subject. Since the pulse oximeter can detect the waves R shown in FIG. 5, the pulsation period T can be detected in the same manner as in the case of the electrocardiograph. However, the pulse oximeter measures the oxygen saturation degree through a fingertip, the detected pulsation period T lags behind the actual pulsation period. Further, since the flowability of blood in a vessel changes for each person and the pulsation-period lag occurs due to the body, the standstill period cannot be uniformly determined.

Next, the rotation-time calculation unit 18 calculates a rotation time period S of the rotation table 4 based on the pulsation period T, where the equation:

$$S = nT \qquad (1)$$

where n indicates an odd number. The rotation time period per rotation of the subject P is empirically determined to be 3 seconds $\leq t \leq 10$ seconds. A too short rotation time period S causes the body motion due to dizziness and too long rotation time period causes the body motion due to exhausted patience. Subsequently, an artifact is created in the reconstructed image. Although plural 'n's satisfying the expression 3 seconds $\leq t \leq 10$ seconds often exist, in exemplary embodiments n is selected according to the age of the subject P (step S105).

Once the rotation time period S is determined, a message is displayed on the interface unit 16, so as to show that the photographing preparation is finished, and an instruction to start photographing is issued. Then, the rotation table 4 starts rotating according to an instruction transmitted from the control unit 12 (step S106). The control unit 12 monitors an encoder signal transmitted from the rotation table 4 and determines that the predetermined speed and angle are attained. The encoder signal is used for determining the data integration timing.

Where the rotation of the rotation table 4 attains the predetermined speed and angle, a signal is transmitted to the X-ray generator 1 and the X-ray generator 1 starts X-ray exposure. Where the rotation table 4 rotates at the predetermined rotation angle and a predetermined number of views, that is, the projection number is attained, the control unit 12 issues an instruction to the X-ray generator 1, so as to stop the X-ray exposure. Then, the control unit 12 reduces the rotation speed until the rotation table 4 stops (step S107).

When using an encoder generating 25,000 pulses per rotation of the rotation table 4, the two-dimension detector 3 collects data for each pulse of an encoder signal for collecting projection data of one thousand views per rotation. The control unit 12 counts the encode-pulse number and generates an integration signal for every twenty-five pulses and calculates the amount of X-rays that reached the two-dimension detector 3.

Although X-rays are successively generated in this embodiment, an X-ray may be generated in a pulse-like manner so that the generated X-ray is synchronized to an integration section of the two-dimension detector 3 based on the encoder signal, without being limited to the above-described configuration. Data transmitted from the two-dimension detector 3 is transferred to the reconstruction unit 5 in succession via the bus 11. The data transfer is continued until the rotation table 4 rotates at the predetermined rotation angle and the predetermined number of views are collected. The last projection data is collected soon after the X-ray exposure is finished.

The motion area C is detected after the scan data of the subject P is collected (step S108). The collected full data A is analyzed by the motion-area detection unit 19. The analysis is performed to determine which part of the full data A can be used for the full-scan reconstruction and which part thereof can be used for the half-scan reconstruction.

More specifically, the analysis is performed for dividing the full data A into the motion area C showing the motion of the body or internal organ and the standstill area B showing no motion. The reconstruction unit 5 rearranges the projection data of a subject area corresponding to the motion area C, so as to make the projection data ready for half scanning, and performs reconstruction. Further, the reconstruction unit 5 reconstructs the projection data corresponding to the standstill area B by full scanning.

The reconstruction unit 5 performs preprocessing, filtering, and reverse projection. The preprocessing includes offset processing, LOG conversion, gain correction, and defect correction. Since a Ramachandran function and a Shelpp-Logan function are frequently used for the filtering, they are used in this embodiment. Filtered data is reversely projected, where the Feldkamp algorithm is used from the filtering to the reverse projection. When the reverse projection is finished and a cross-section image obtained by the CT apparatus is reconstructed, the cross-section image is displayed on the image display unit 14.

Although the Feldkamp algorithm is used here, as the reconstruction algorithm, the present invention can be achieved without being limited to the above-described embodiment. For example, a known example is disclosed in "Practical Cone-Beam Algorithm", by Feldkamp, Davis, and Kress, *J. Opt. Soc. Am. A*1, 612 to 619, 1984.

The type of processing performed thereafter changes according to whether or not the motion area C exists in the data. Where the motion-area detection unit 19 detects the motion area C (as determined in step S116), the data corresponding to the detected area in the full data A is rearranged (step S109). The initial value of the standstill period Q obtained at step S104 is used for the rearrangement. When using the pulse oximeter, which phase of the pulsation period T should be determined to be the initial value of the standstill period Q is determined by determining a statistically high-incidence value based on information about the age, height, and so forth of the subject P.

In general, the phase difference between the wave R of the electrocardiograph and that of the pulse oximeter increases with increases in the age of the subject P, since aging causes artery hardening. The phase difference also increases with the height of the subject P, since the length of vessels in which blood flows increases with the height. The data rearrangement is performed according to the standstill period Q (step S109) and a half-scan image is reconstructed by using the rearranged scan data (step Silo).

As described above, the first reconstructed image is created by using the data that is rearranged based on the initial value of the standstill period Q. Therefore, the first reconstructed image may include an artifact generated by the pulsation change. Therefore, the reconstructed image has to be evaluated (step Sill). The evaluation may be performed by a person, but can be automated. In the case where the person performs the evaluation, he/she evaluates whether or not the artifact occurs in part around the heart of the reconstructed image. Where the artifact is identified, an instruction to make a retry is issued and a modification is made to the standstill period Q according to the instruction (step S112).

The modification to the standstill period Q is made by successively shifting the phase of the standstill period Q in the pulsation period T. The step width of shifting may be arbitrarily selected, so long as the value is substantially one-tenth of the pulsation period T. Then, the data rearrangement of the step S109 is performed again according to the modification to the standstill period Q and a reconstructed image is created (step S110). The above-described loop is repeated until the reconstructed image becomes acceptable relating to the artifact.

Where the retry is selected, the data rearrangement (step S109), the half-scan reconstruction (step S110), and the image evaluation (step S111) are performed again. Where the result of image evaluation is successful, the three-dimension voxel E corresponding to the motion area C is coupled to the three-dimension voxel E corresponding to the standstill area B.

As for the standstill area B determined by the motion-area detection unit 19, image reconstruction is performed by using the full-scan data (step S113). Where the three-dimension voxel E of the motion area C is coupled to that of the standstill area B (step S114), a coupled three-dimension reconstructed image is displayed and the photographing is finished (step S115).

In the case of the above-described automated reconstructed-image evaluation, first, an area around the heart is specified, the distribution of images of the area is calculated, and the distribution value is compared to a predetermined value. The image to be cut may be specified by an operator based on obtained tomography images, or automatically specified by performing heart-portion determination processing. The heart-portion determination processing may be performed by specifying a predetermined area estimated based on the figure of the subject P, or using pattern identification.

Figure 6:
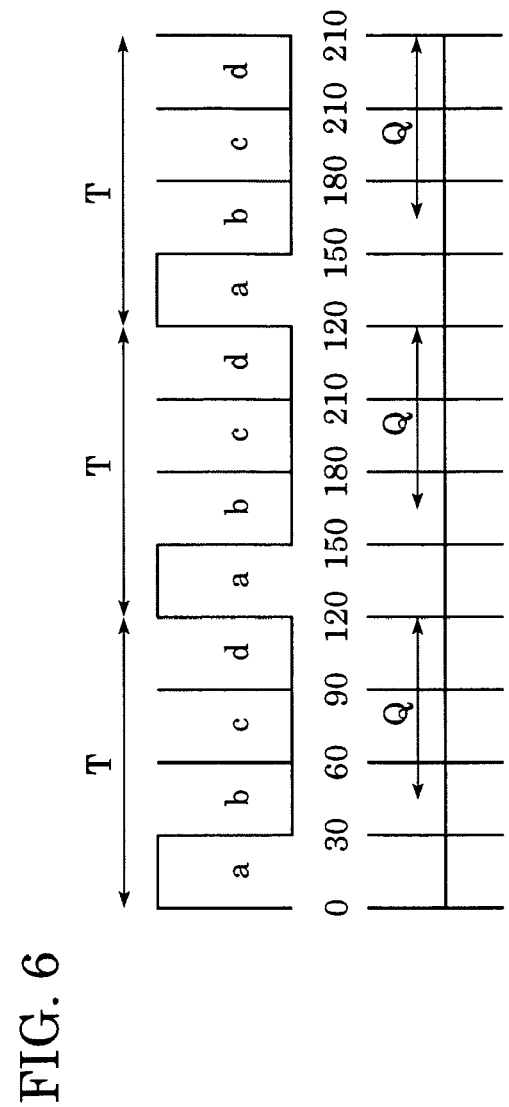
FIG. 6 shows the relationship between a pulsation period and a standstill period for scan data.

FIG. 6 is a time chart showing the relationship between the pulsation period T and the scan data, where the photographing is finished in a time period three times as long as the pulsation period T. This relationship is expressed by the equation:

$$S=3T \qquad (2)$$

where the letter S denotes the rotation time period. The numerical values shown on the middle row shown in this drawing indicate the projection angles, the data of a 120-degree section is collected for every pulsation period T. Here, the pulsation period T is divided into four sections a, b, c, and d. For example, the section a corresponds to the contraction period and the sections b to d substantially correspond to a relaxation extension period, and the standstill period Q functioning as the precondition of the data rearrangement of step S109 is set to a section indicated by an arrow, as shown in FIG. 6. Here, the length of the standstill period Q is determined to be sixty percent of the pulsation period T. The length rate of the standstill period Q is usually determined to be sixty to seventy percent. The artifact decreases with decreases in the rate.

Figure 7:
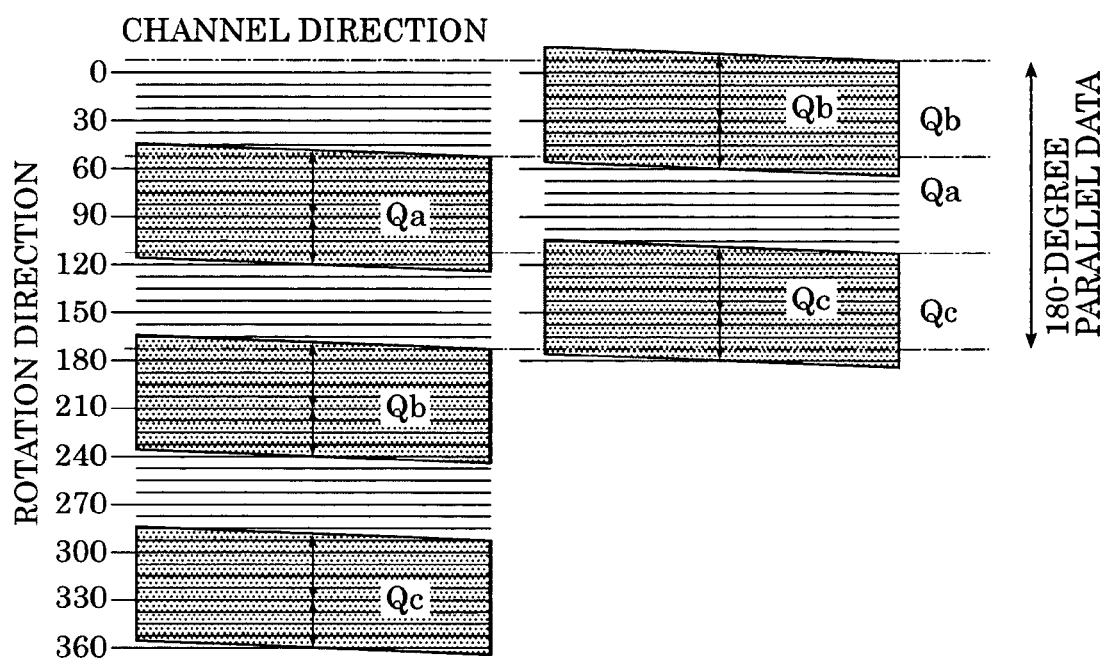
FIG. 7 illustrates processing performed for rearranging standstill sections in full-scan data, so as to generate half-scan data.

Three parallelograms Qa, Qb, and Qc shown on the left column of FIG. 7 illustrate the standstill period Q, where the rotation table 4 rotates at a 360-degree angle. The parallelogram Qa corresponds to the first standstill section Q shown in FIG. 6, the parallelogram Qb corresponds to the standstill section Q shown in the middle, and the parallelogram Qc corresponds to the last standstill section Q. Since the collected data is fan data, the areas of collected data are represented, as parallelograms. In FIG. 7, the degree of fan angle is expressed by the equation $\phi=7.2$.

In the right column of FIG. 7, the data of the standstill sections Qb and Qc is folded at an angle of 180°. Where the data of the standstill periods Qb, Qa, and Qc is rearranged in that order, parallel data corresponding to a 180° angle is generated. The following equation must be satisfied, as the conditions for creating the 180°-angle parallel data on the right column shown in FIG. 7, where the ratio of standstill section Q is represented by the letter p. Further, the letter n shown in the following equation must be an odd number.

$$P=(180+n\phi)/360 \qquad (3)$$

As is clear from FIG. 7, where the letter n is an even number and the data is folded over at a 180° angle, the data overlaps one another, so that missing data cannot be redeemed by folding. For example, where the equation p=0.6 and the equation n=3 hold, the degree of fan angle $\phi$ is determined to be 12°. Further, where the equation p=0.6 and the equation n=5 hold, the degree of fan angle $\phi$ is determined to be 7.2°.

Figure 8:
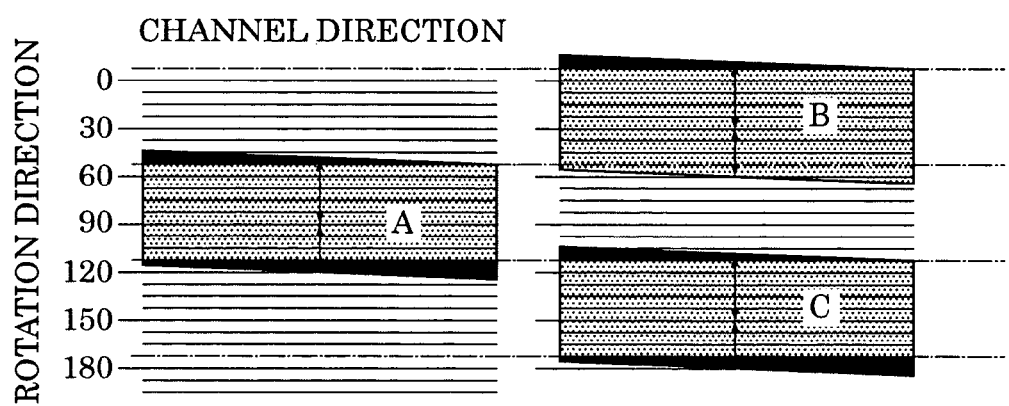
FIG. 8 illustrates a weight-assigning coefficient used for reconstruction by using half-scan data.

FIG. 8 shows that the data arrangement can be performed according to two methods. According to one of the methods, parallel data corresponding to data part shown in FIG. 8 from which highly-colored triangle portions are removed is created. This method is known, as the fan/parallel conversion, and disclosed in Japanese Patent Application No. 9-235566 and Japanese Patent Laid-Open No. 11-76227.

According to the other method, the data rearrangement is not actually performed. The fan data is weighted when it is reversely projected, and reconstruction is performed. This weighting reconstruction is a method used for performing reconstruction by using half-scan data collected by a fan beam. Each of the highly-colored triangle portions shown in FIG. 8 has a weight of zero and is reversely projected. The other portion has a weight of one and is reversely projected. The weighting reconstruction method is disclosed in detail in paragraph [0043] of Japanese Patent Laid-Open No. 6-209927 and paragraph [0023] of Japanese Patent Laid-Open No. 11-9589.

Next, FIG. 8 shows a method for specifying the conceptually illustrated triangle data areas that have the weight of zero and are reversely projected. Where the odd number n and the fan angle φ are determined according to the equation p=(180+nφ)/360, p is determined. For example, where the equation n=3 and the equation φ=7.2 hold, the equation p=0.56 holds. That is to say, where the standstill section Q is set so that the ratio p is equivalent to 0.56, the triangle data areas that have the weights of zero and are reversely projected can be obtained by removing a rectangle from each of the parallelograms Qa to Qc.

Figure 9A:
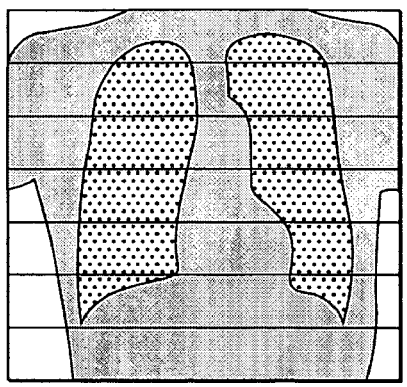
FIG. 9 illustrates a motion-area detection method.
Figure 9B:
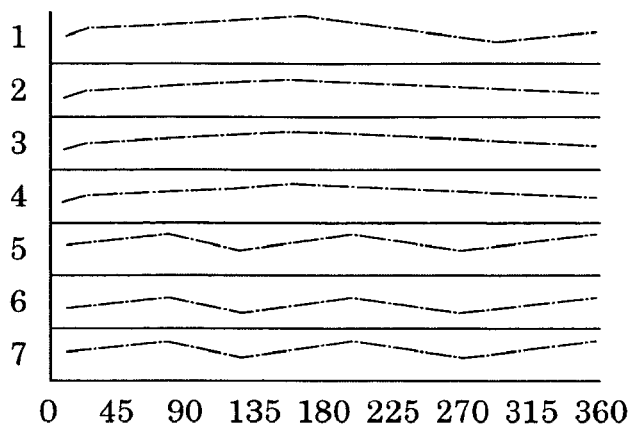

The motion-area detection unit 19 will now be described in detail. A first method is a method similar to the method disclosed in Japanese Patent Laid-Open No. 2002-355241. FIG. 9A shows example projection data obtained for a single direction. For simplicity, the image shown is obtained by accidentally photographing the chest from the front. FIG. 9B is a graph obtained by dividing the image into seven strips along the direction of the Z axis or the body axis and calculating the square average (hereinafter referred to as the differential average) of differential images before/after rotation between the divided images.

The patterns shown in the differential-average graph of the divided images 1 to 7 indicate that the subject P is oblong in cross section. The patterns of the divided images 1 to 7 show the heart pulsation. Where the divided image 1 is compared to the divided image 2, patterns corresponding to 0-degree to 225-degree of the divided image 1 are similar to those of the divided image 2. However, the other patterns of the divided image 1 are different from those of the divided image 2, which indicates that body motion occurs in an area of the divided image 1.

Figure 10:
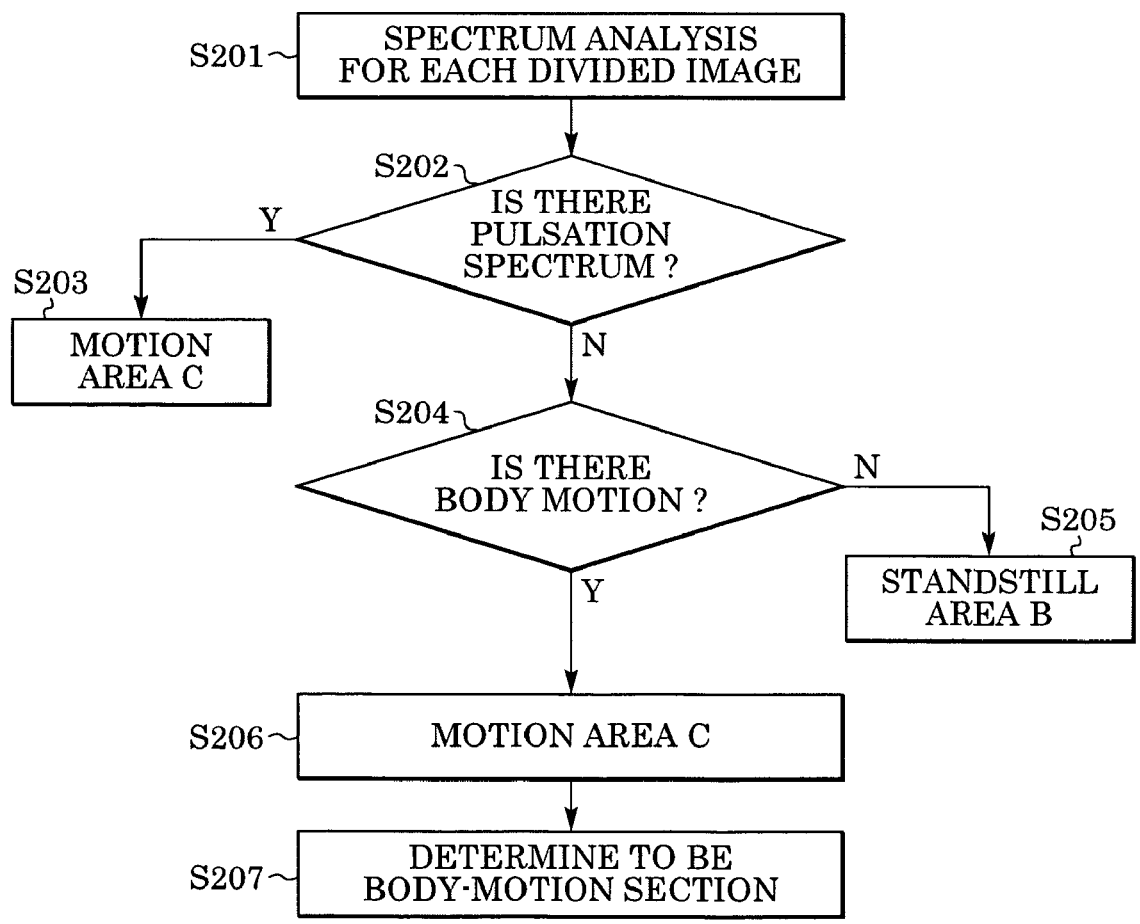
FIG. 10 is a flowchart illustrating motion-area detection.
Figure 11:
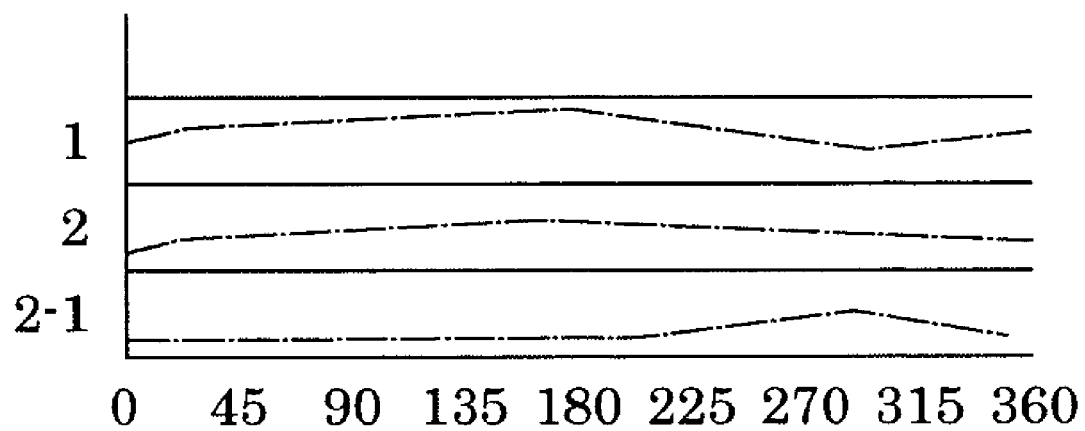
FIG. 11 illustrates a method for detecting a body-motion area.

FIG. 10 is a flowchart showing processing procedures performed for detecting the existence of a periodical motion such as pulsation, or the body motion in the differential-average graph of the divided images. The spectrum analysis is performed by Fourier transform or the like for each of the divided images (step S201). Where the possibility of the heart pulsation is detected, it is checked whether or not a spectrum having a period of from 0.75 to 1.5 seconds exists (step S202). Where the spectrum exists, the divided image is determined to be the motion area C (step S203).

Where no spectrum showing the heart pulsation is detected, it is checked whether or not the body motion exists (step S204). The body-motion detection is performed by comparing the differential average corresponding to 0-degree and that corresponding to 360-degree. Where the value of the difference between the differential averages is lower than a predetermined threshold value, it is determined that the continuity is maintained, that is, no body motion occurs. Where no body motion is detected, the corresponding divided image is determined to be the standstill area B (step S205).

Where body motion is detected, the divided image area is determined to be the motion area C (step S206). The divided image determined to be the motion area C due to the body motion is further subjected to the body-motion section determination (step S207). According to the determination result, half data D is determined from the full data A, so as not to include the body-motion section. Therefore, where any of the other divided images is determined to be the standstill area B, the differential-average differences between the divided images are calculated, as shown in FIG. 11. According to the example shown in FIG. 11, no difference occurs up to 200 degrees and differences occur from 200 to 360 degrees. More specifically, the half data D is created in a section where the differential-average difference values are constantly maintained at the level of 180 degrees+fan angle.

Next, where the other divided image includes no divided area determined to be the standstill area B, the consecutive sections corresponding to the level of 180 degrees+fan angle are shifted, as is the case with the method disclosed in Japanese Patent Laid-Open No. 2000-217810. Then, the quality of the reconstructed image corresponding to each shifting is confirmed so that half data is determined.

The object of the present invention can be achieved by supplying a storage medium storing program code of software for implementing the functions of the above-described embodiments to a system or an apparatus so that a computer (CPU (central processing unit), MPU (micro-processing unit), etc.) of the system or the apparatus reads and executes the program code stored in the storage medium.

In that case, the program code itself, read from the storage medium, achieves the functions of the above-described embodiments.

The storage medium for providing the program code may be, for example, a ROM (read-only memory), a floppy disk, a hard disk, an optical disk, a magneto-optical disk, a CD-ROM (compact disk—ROM), a CD-R (CD—recordable), a magnetic tape, a non-volatile memory card, etc.

Furthermore, not only by the computer reading and executing the program code, but also by the computer executing part of or the entire process utilizing an OS, etc. running on the computer based on instructions of the program code, the functions of the above-described embodiments may be achieved.

Figure 4:
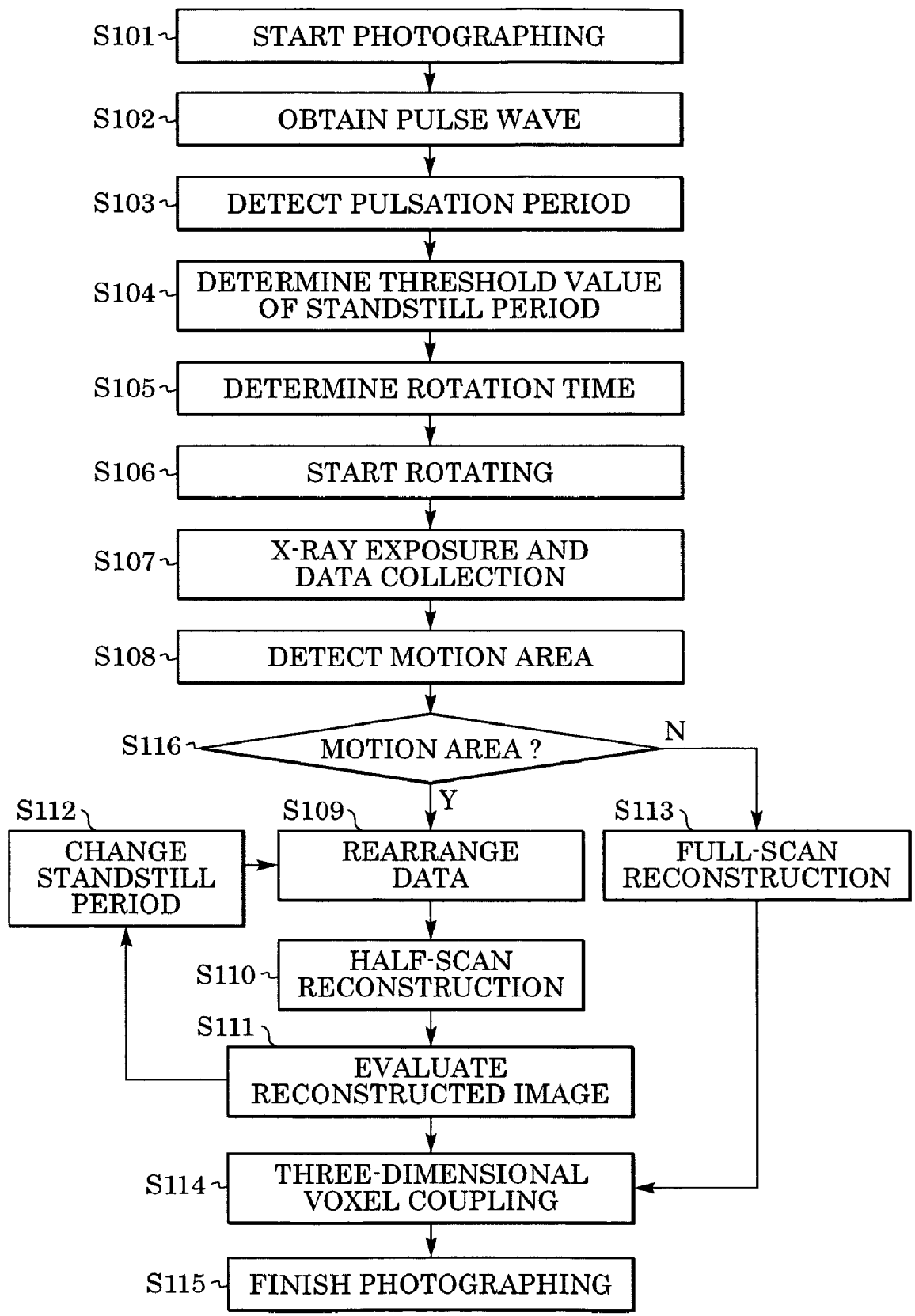
FIG. 4 is a flowchart for performing the embodiment.

Further, in another embodiment of the present invention, the program code read from the storage medium may be written into a memory of a function extension board inserted in the computer or a function extension unit connected to the computer. The functions of the above-described embodiments may be realized by executing part of or the entire process by a CPU, etc. of the function extension board or the function extension unit based on instructions of the program code.

Where the present invention uses the above-described program or storage medium storing the program, the program includes program codes complying with the flowcharts shown in FIGS. 4 and 10, for example.

As has been described, the present invention allows determining an area generating an artifact caused by the heart pulsation or the like, or a body-motion area, with reference to an image. Subsequently, only half-scan data generating no artifacts or a small number of artifacts is extracted from collected full-scan data. The extracted half-scan data is reconstructed and an image with a suitable S/N (signal-to-noise) ratio is obtained.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2004-28891 filed on Feb. 5, 2004, which is hereby incorporated by reference herein.

What is claimed is:

1. An X-ray image processing method for creating three-dimension reconstructed image data by using plural projection image data, the X-ray image processing method comprising:

a division step for dividing an area corresponding to the projection image data into at least one standstill area showing no body motion and at least one motion area showing body motion based on the projection image data;

a reconstruction step for creating the three-dimension reconstructed image data by using the projection image data; and a displaying step for displaying the reconstructed standstill area and motion area, wherein reconstruction for the standstill area is performed by full scanning by using the projection image data corresponding to 360-degree photographing directions, and reconstruction for the motion area is performed by half scanning by using the projection image data corresponding to 180-degree photographing directions.

2. The X-ray image processing method according to claim 1, wherein, in the reconstruction step, the projection image data showing no body motion is selected and reconstructed for the motion area.

3. The X-ray image processing method according to claim 1, wherein, in the reconstruction step, reconstruction is performed by selecting the projection image data based on a heart-pulsation standstill period.

4. The X-ray image processing method according to claim 1, wherein the plural projection image data is picked up, so as to satisfy the following equation:

$$p=(180+n\phi)/360,$$

where p denotes a ratio of a single heart-pulsation period to a single standstill period, n denotes an odd number, and $\phi$ denotes a fan angle.

5. The X-ray image processing method according to claim 1, further comprising a coupling step for coupling three-dimension voxel data obtained by the full-scan reconstruction to three-dimension voxel data obtained by the half-scan reconstruction.

6. A computer readable storage medium storing a program for making a computer perform an X-ray image processing method for creating three-dimension reconstructed image data by using plural projection image data, the X-ray image processing method comprising:

a division step for dividing an area corresponding to the projection image data into at least one standstill area showing no body motion and at least one motion area showing body motion based on the projection image data;

a reconstruction step for performing reconstruction for the standstill area by full scanning by using the projection image data corresponding to 360-degree photographing directions;

a reconstruction step for performing reconstruction for the motion area by half scanning by using the projection image data corresponding to 180-degree photographing directions; and a displaying step for displaying the reconstructed standstill area and motion area.

7. An X-ray image processing apparatus comprising:

an X-ray generator for generating at least one X-ray;

a rotation table for rotating a subject in the X-ray image processing apparatus such that the at least one X-ray generated by the X-ray generator passes through the subject;

a two-dimension detector for converting the X-ray passed through the subject into projection image data;

a division unit for dividing an area corresponding to the projection image data into at least one standstill area showing no body motion and at least one motion area showing body motion based on projection image data picked up by the two-dimension detector; and a reconstruction unit for creating three-dimension reconstructed image data by using the projection image data, wherein reconstruction for the standstill area is performed by full scanning by using the projection image data corresponding to 360-degree photographing directions, and reconstruction for the motion area is performed by half scanning by selecting the projection image data corresponding to 180-degree photographing directions.

8. An image processing system, wherein the X-ray image processing apparatus according to claim 7 is connected to at least one of an image display and a file server via a network.

* * * * *